United States Patent
Yamanaka et al.

(10) Patent No.: US 11,141,137 B2
(45) Date of Patent: Oct. 12, 2021

(54) ULTRASONIC IMAGING DEVICE AND IMAGE PROCESSING DEVICE

(71) Applicant: Hitachi, Ltd., Tokyo (JP)

(72) Inventors: Kazuhiro Yamanaka, Tokyo (JP); Kenichi Kawabata, Tokyo (JP)

(73) Assignee: HITACHI, LTD., Tokyo (JP)

( * ) Notice: Subject to any disclaimer, the term of this patent is extended or adjusted under 35 U.S.C. 154(b) by 305 days.

(21) Appl. No.: 16/381,037

(22) Filed: Apr. 11, 2019

(65) Prior Publication Data

US 2020/0008784 A1    Jan. 9, 2020

(30) Foreign Application Priority Data

Jul. 5, 2018    (JP) .............................. JP2018-128519

(51) Int. Cl.
- *A61B 8/08* (2006.01)
- *G01S 15/89* (2006.01)
- *G01S 7/52* (2006.01)

(52) U.S. Cl.
CPC .......... *A61B 8/5253* (2013.01); *A61B 8/5269* (2013.01); *G01S 7/5209* (2013.01); *G01S 15/8915* (2013.01); *G01S 15/8995* (2013.01)

(58) Field of Classification Search
CPC ....... A61B 8/5253; A61B 8/5269; A61B 8/14; A61B 8/15; A61B 8/5207; A61B 8/4494; A61B 8/4488; A61B 8/4477; A61B 8/0825; A61B 8/406; A61B 8/5238; G01S 7/5209; G01S 15/8915; G01S 15/8995; G01S 15/8913; G01S 7/52038; G01S 15/8929; G01S 15/8945; G01S 15/8993; G01S 15/8922; G01S 7/52077
See application file for complete search history.

(56) References Cited

U.S. PATENT DOCUMENTS

| | | | |
|---|---|---|---|
| 6,464,638 B1 | 10/2002 | Adams et al. | |
| 10,101,450 B2 * | 10/2018 | Asaka | G01S 15/8952 |
| 2008/0242992 A1 * | 10/2008 | Criton | G01S 15/8927 |
| | | | 600/447 |

(Continued)

FOREIGN PATENT DOCUMENTS

JP    2007-222264 A    9/2007

OTHER PUBLICATIONS

He, et al., "Guided Image Filtering," IEEE Transactions on Pattern Analysis and Machine Intelligence, vol. 35, No. 6, Jun. 2013, pp. 1397-1409.

*Primary Examiner* — Keith M Raymond
*Assistant Examiner* — Nicholas A Robinson
(74) *Attorney, Agent, or Firm* — Mattingly & Malur, PC

(57) ABSTRACT

The invention is to provide an ultrasonic image with a clear tissue structure while reducing speckle noise of the ultrasonic image. An ultrasonic wave is transmitted from the transducer to the subject, and an echo generated in the subject is received. The first ultrasonic image and the second ultrasonic image are generated using a reception signal. The second ultrasonic image is an image smoother than the first ultrasonic image. The image processing unit calculates filter coefficients using pixel values of corresponding pixels of the first ultrasonic image and the second ultrasonic image, and generates an output image by processing one of the first ultrasonic image and the second ultrasonic image using the filter coefficients.

8 Claims, 9 Drawing Sheets

(56) References Cited

U.S. PATENT DOCUMENTS

| | | | |
|---|---|---|---|
| 2013/0245445 A1* | 9/2013 | Kakee | A61B 8/54 600/440 |
| 2013/0301380 A1* | 11/2013 | Oraevsky | A61B 8/5261 367/7 |
| 2018/0271480 A1* | 9/2018 | Kawabata | A61B 8/543 |

* cited by examiner

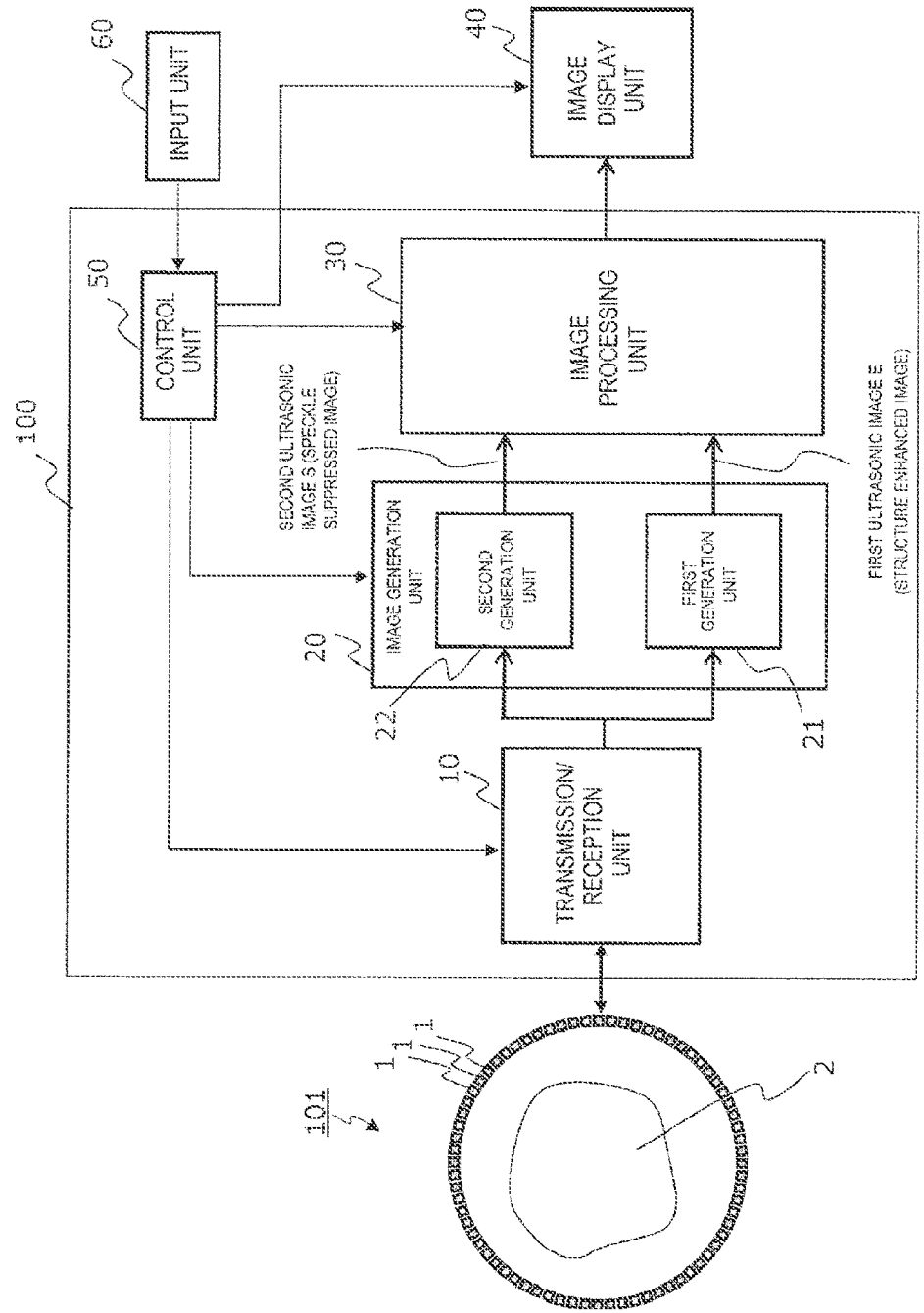
[FIG. 1]

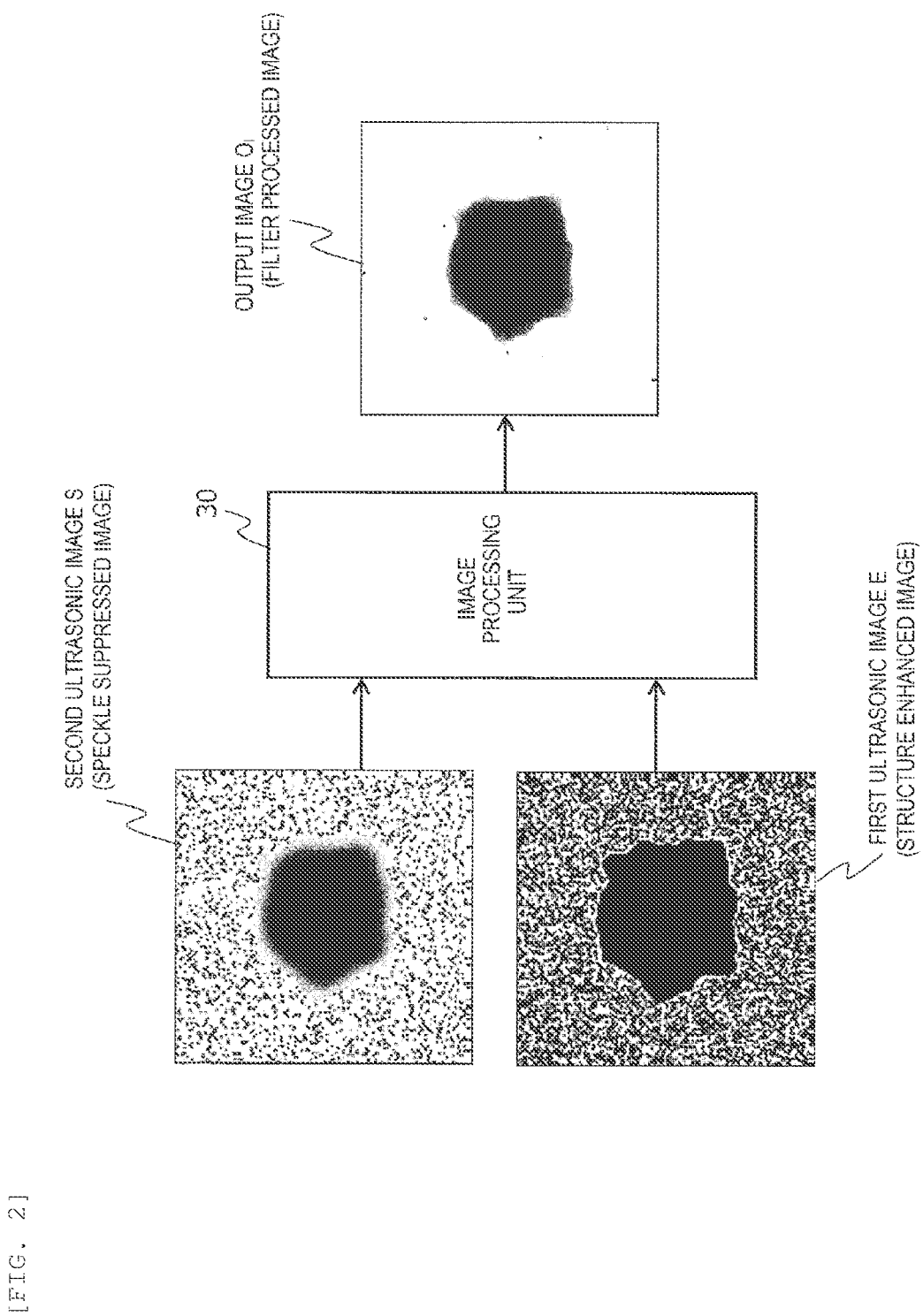

FIG. 3(A)
FIG. 3(B)
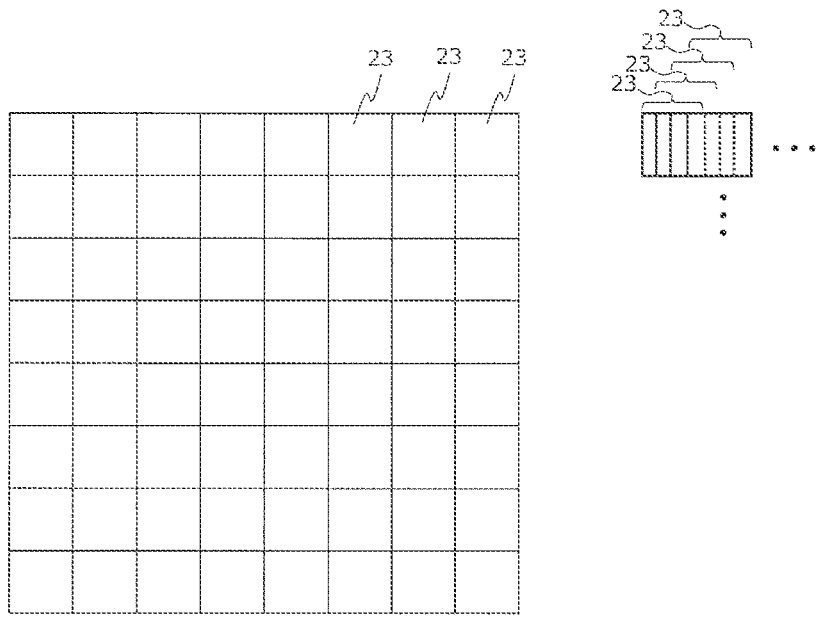
[FIG. 4]
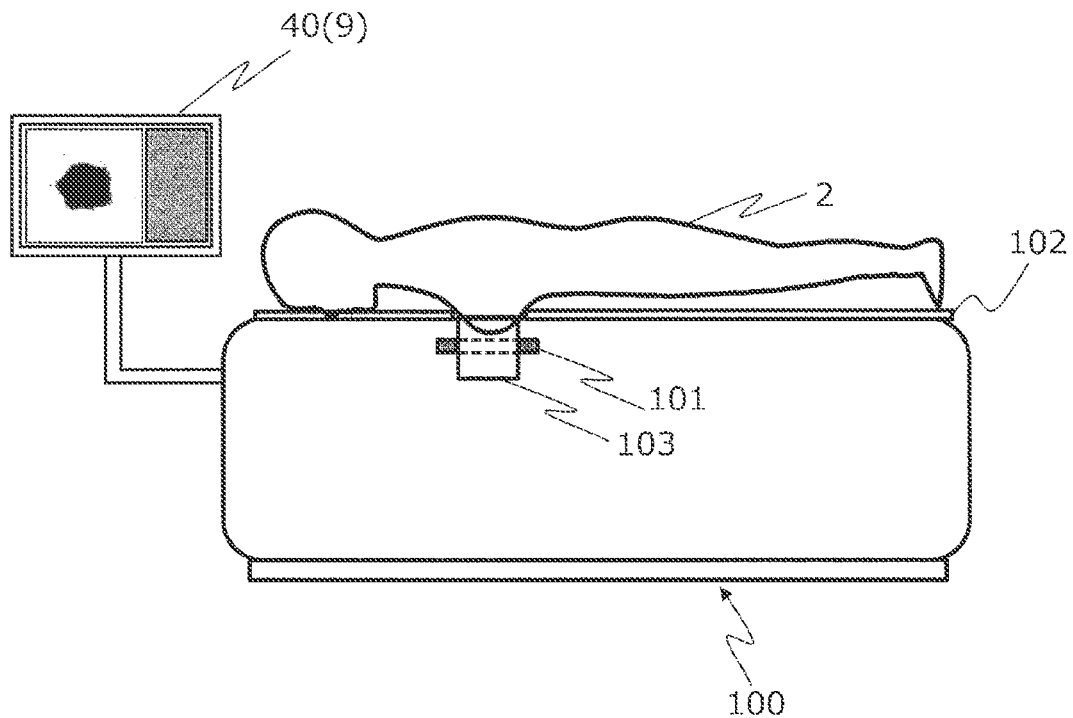

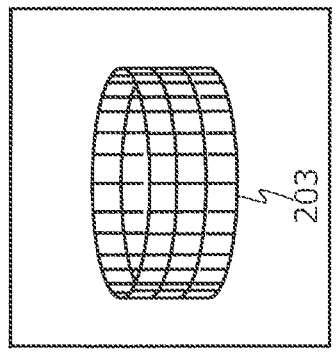
FIG. 5(C)
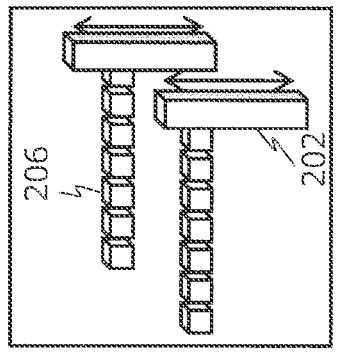
FIG. 5(F)
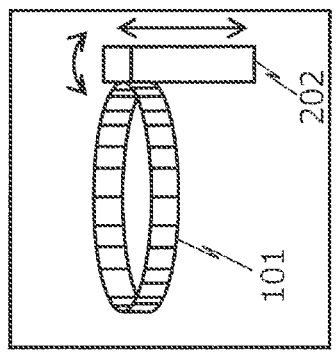
FIG. 5(B)
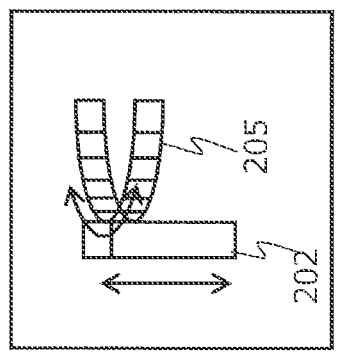
FIG. 5(E)
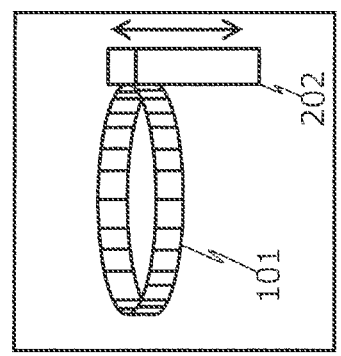
FIG. 5(A)
FIG. 5(D)

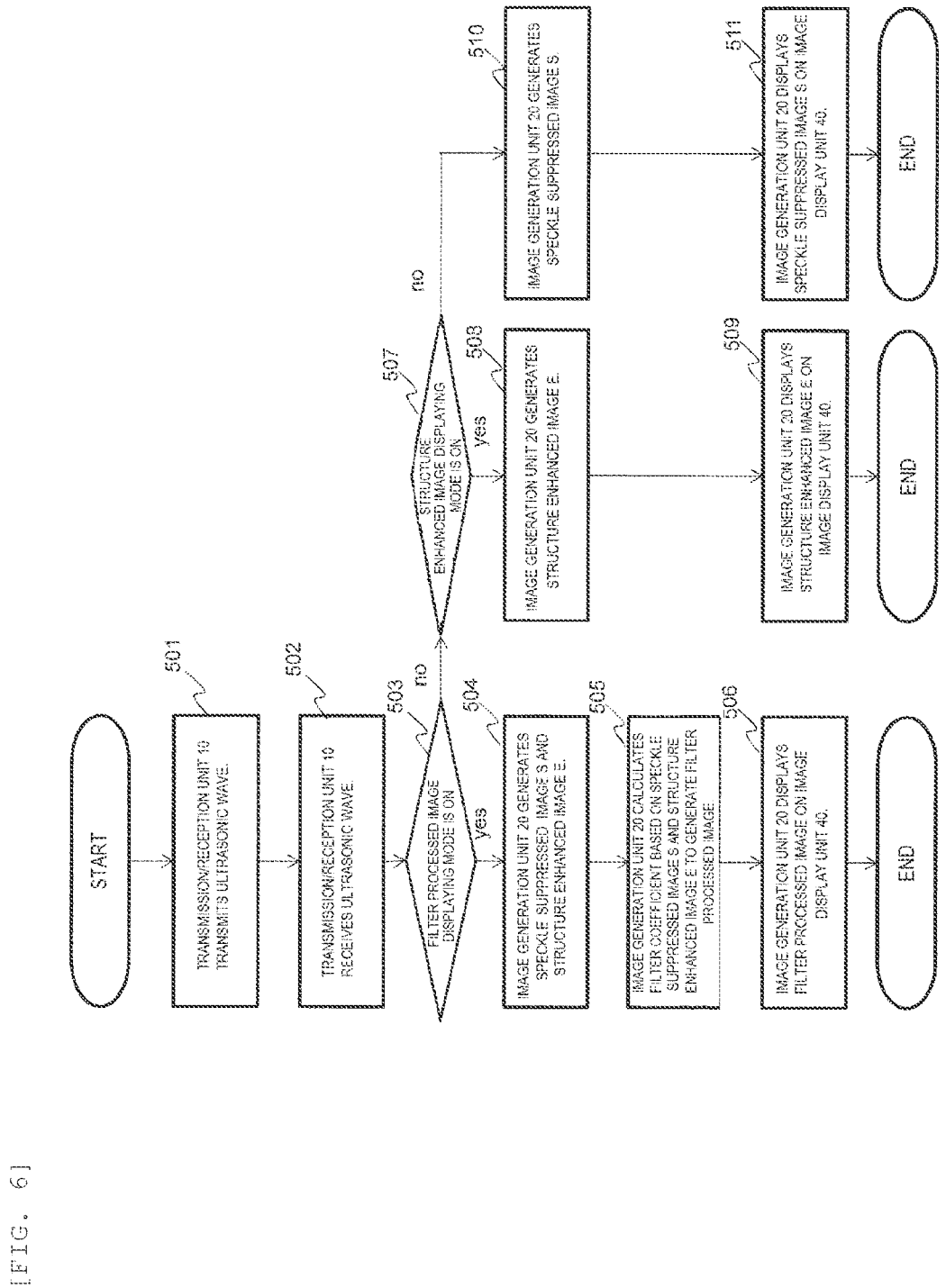
[FIG. 6]

[FIG. 7]
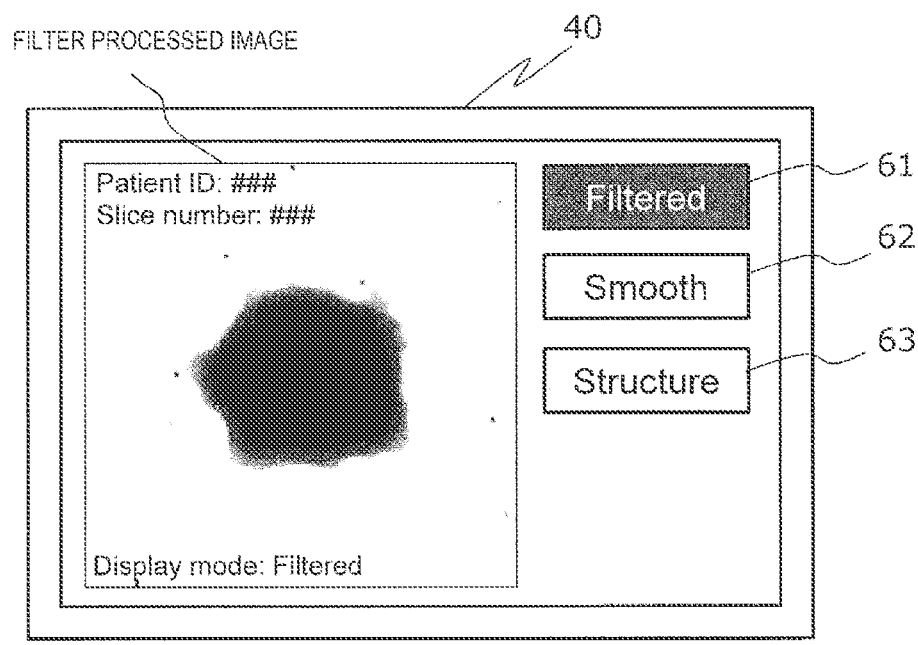
[FIG. 8]
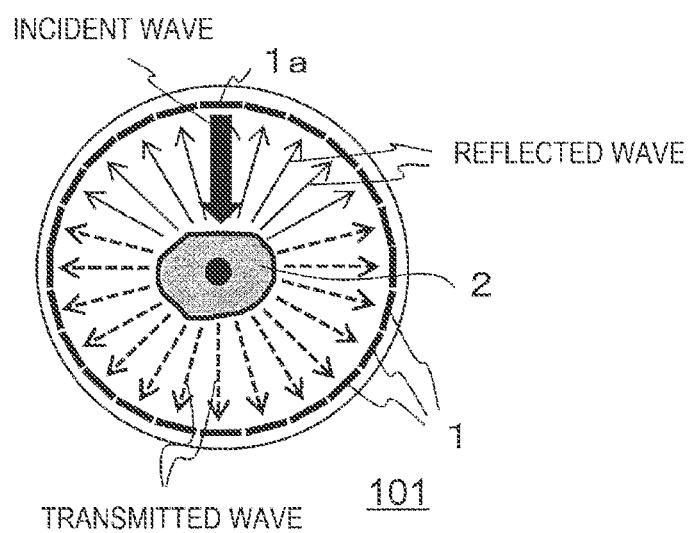

[FIG. 9]
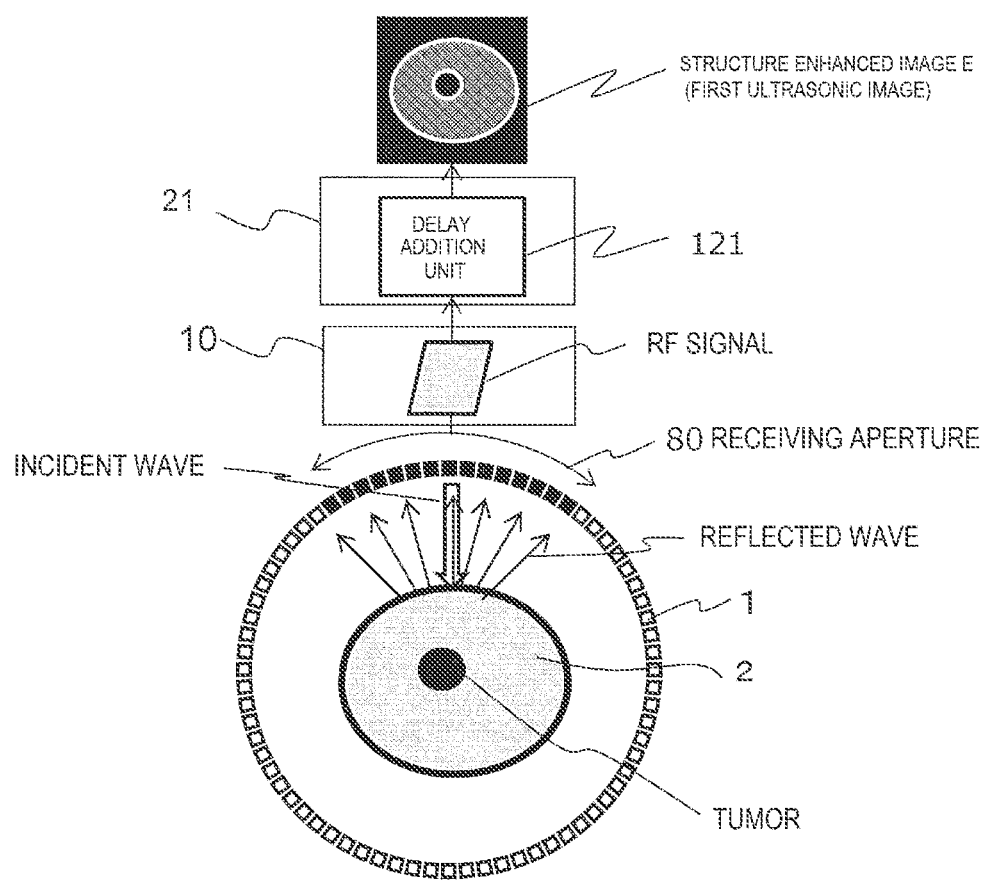

[FIG. 10]
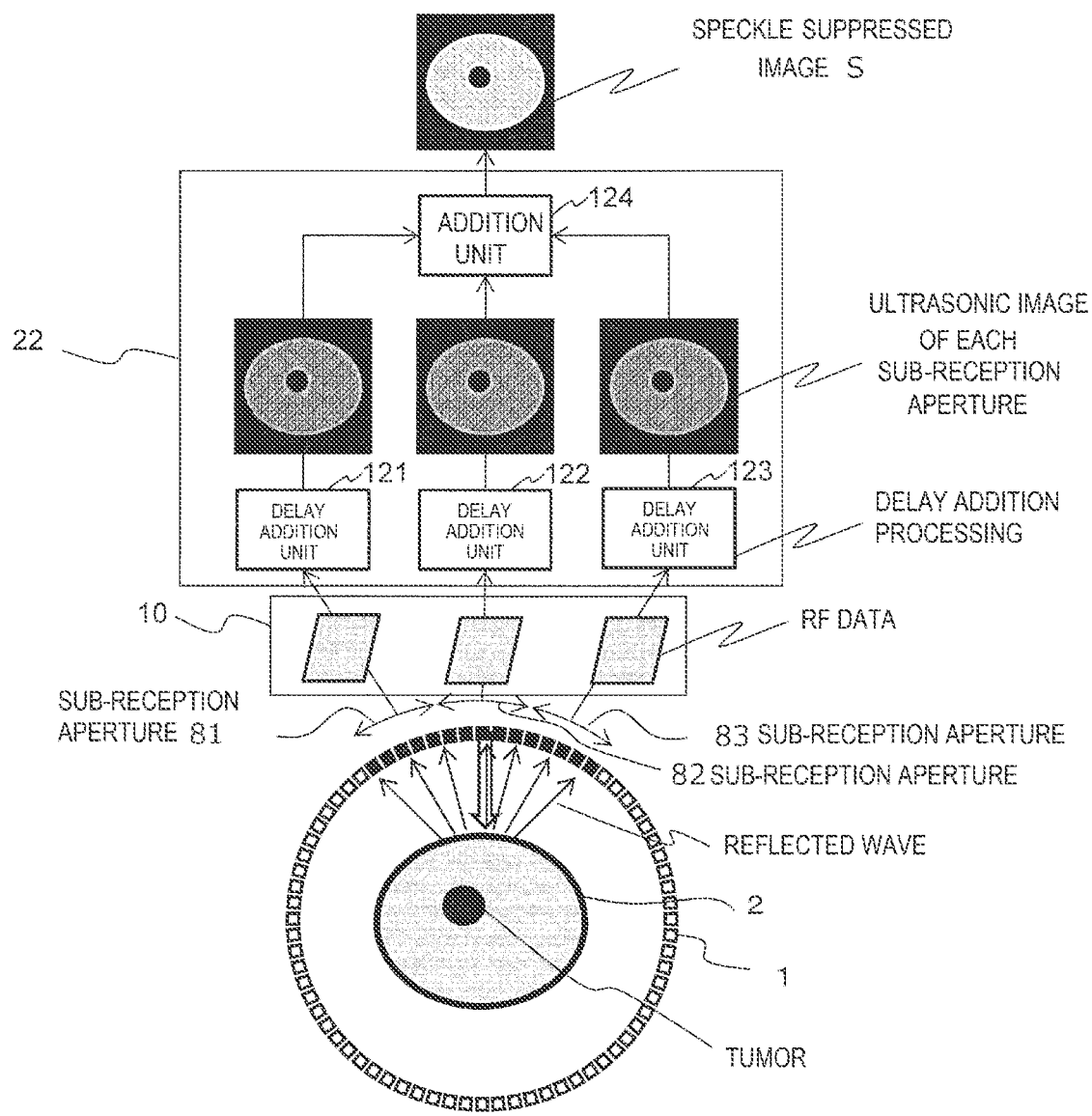

[FIG. 11]
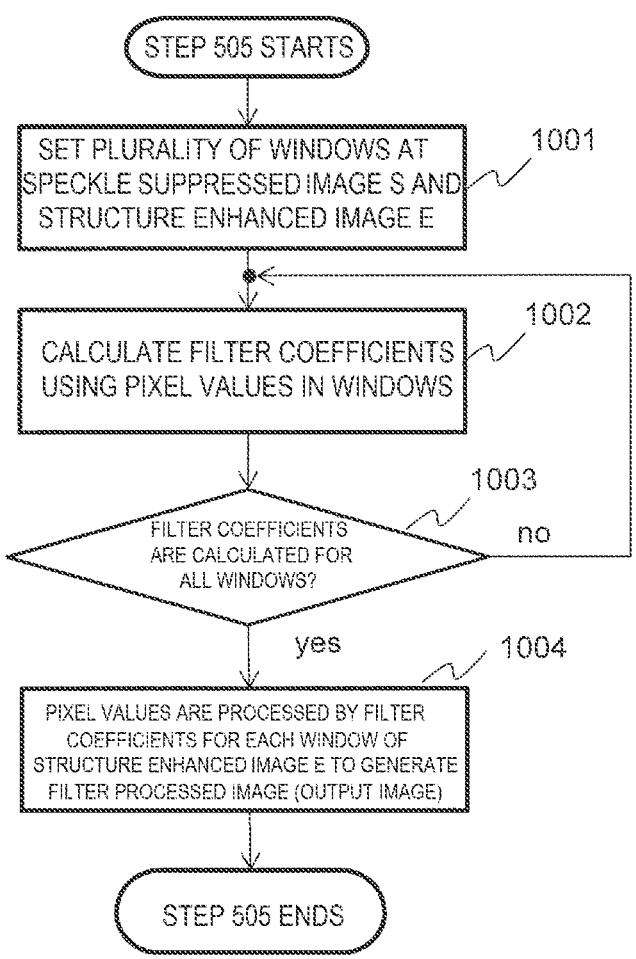

ULTRASONIC IMAGING DEVICE AND IMAGE PROCESSING DEVICE

CROSS-REFERENCE TO RELATED APPLICATION

The present application claims priority from Japanese application JP 2018-128519, filed on Jul. 5, 2018, the contents of which is hereby incorporated by reference into this application.

TECHNICAL FIELD

The present invention relates to an ultrasonic imaging device that generates an image with reduced speckle noise.

BACKGROUND ART

In the ultrasonic imaging device, a configuration is widely used in which an image is reconstructed by transmitting an ultrasonic wave from a probe to a subject, receiving a reflected wave (echo) generated in the subject by a probe, and performing phase addition on an obtained reception signal by a delay addition method for each desired reception focus. It is known that "speckle" is generated in the image (ultrasonic echo image) obtained as described above. The speckle is generated by interference between ultrasonic waves reflected by countless scattering points in the subject, and does not reflect a tissue structure itself. Therefore, when the user attempts to read the tissue structure from the ultrasonic echo image, the speckle becomes a noise.

A spatial compound method is used as an effective method of reducing speckle of the ultrasonic image. This method includes performing a plurality of transmission/reception in which the transmission/reception angle of the ultrasonic beam to an imaging object is changed, obtaining the luminance image for each of the plurality of transmission/reception with different transmission/reception angles of the ultrasonic beam and then synthesizing an obtained luminance image in an incoherent manner. The speckle pattern of the luminance image obtained by each transmission/reception is slightly different because the angle of the ultrasonic beam is different, and the speckle pattern can be reduced by combining the luminance images. For example, in the spatial compound method disclosed in Patent Literature 1, a plurality of images with different reception angles are obtained by a multi-look process in which the long axis aperture of the probe is not changed and a reception aperture in the short axis direction (elevation direction) is reduced (changed) to a plurality of types at the time of reception when transmitting/receiving the plurality of ultrasonic beams.

As another method of reducing the speckle, Patent Literature 2 discloses a technique of reducing speckle while performing a boundary enhancement by preparing two images obtained by applying a smoothing processing and a boundary enhancement processing on ultrasonic echo images respectively, and weighting and combining the two images in pixel units respectively.

On the other hand, non-Patent Literature 1 proposes a principle of a novel image filter processing called a guided filter. In this guided filter processing, a guide image is used in addition to an input image which is a filtering object, and a window is set at a corresponding position of these images. When the pixel value of the i-th pixel in the window of the guide image is $I_i$, the pixel value of the i-th pixel in the window of the input image is $p_i$, and the i-th pixel value of the output image is $q_i$, the pixel value $q_i$ of the output image is calculated by simultaneously satisfying $q_i = aI_i + b$ and $q_i = p_i - n_i$, and calculating a, b, and n in the window such that $n_i$ becomes the smallest. This guided filter is described in non-Patent Literature 1 as being able to perform an edge-preserving smoothing processing while leaving the contour of the image. Further, non-Patent Literature 1 discloses several examples showing that the image quality of an output image changes depending on the image quality of the guide image.

PRIOR ART LITERATURE

Patent Literature

Patent Literature 1: U.S. Pat. No. 6,464,638 specification
Patent Literature 2: JP-A-2007-222264

Non-Patent Literature

Non-Patent Literature 1: K. He, J. Sun, and X. Tang, "Guided Image Filtering," IEEE Transactions on Pattern Analysis and Machine Intelligence, 35, pp. 1397-1409.

SUMMARY OF INVENTION

Technical Problem

The spatial compound method can reduce or prevent speckles, but when transmitting/receiving a plurality of times, the time required for imaging becomes long. Further, if a body motion or the like of the subject occurs during a plurality times of transmission/reception, a position shift would occur in the tissue of the subject between the obtained plurality of images. When the plurality of images are added in the incoherent manner, the speckle can be reduced or prevented, but the contour of the tissue structure of the subject is blurred. Further, as described in Patent Literature 1, if a multi-look processing of reducing the reception aperture to a plurality of stages is used, a plurality of types of images can be obtained by one time of reception, but in order to reduce the reception aperture, the number of reception signals used to generate one image is reduced, and the resolution of the image is reduced. Therefore, when the plurality of images are added in the incoherent manner, the speckle can be reduced or prevented, but there is a problem that the contour of the tissue structure of the subject is also blurred.

In the technique of weighting and combining a smooth processed image and a boundary enhancement processed image in the pixel units respectively described in Patent Literature 2, it is not easy to set the weighting because the effect of reducing the speckle while performing the boundary enhancement would not be achieved if an appropriate weighting is not performed in the pixel units.

Non-Patent Literature 1 discloses a principle of the guided filter processing and several processing examples, but the application to the ultrasonic image is not disclosed at all. Therefore, it is unclear whether or not the speckle can be reduced by the guided filter processing. When the guided filter processing is applied to the ultrasonic image, it is unclear there is a possibility of being capable of reducing speckle by using which kind of image as the input image and the guide image.

It is an object of the invention to provide an ultrasonic image having a clear tissue structure while reducing the speckle noise of the ultrasonic image.

Solution to Problem

According to the invention, provided is an ultrasonic imaging device that includes a transmission/reception unit which transmits an ultrasonic wave from one or more transducers to a subject by outputting a transmission signal to the one or more transducers, at the same time receives a reception signal output by the plurality of transducers that received an echo generated in the subject and performs a predetermined processing, an image generation unit which generates a first ultrasonic image and a second ultrasonic image using the reception signal processed by the transmission/reception unit, and an image processing unit which generates an output image using the first ultrasonic image and the second ultrasonic image. The image generation unit generates an image smoother than the first ultrasonic image as the second ultrasonic image. The image processing unit generates an output image by calculating filter coefficients using pixel values of corresponding pixels of the first ultrasonic image and the second ultrasonic image, and processing one of the first ultrasonic image and the second ultrasonic image by the filter coefficients.

Advantageous Effect

According to the invention, it is possible to provide an ultrasonic image with a clear tissue structure while reducing the speckle noise of the ultrasonic image.

BRIEF DESCRIPTION OF DRAWINGS

FIG. 1 is a block diagram showing a configuration of the ultrasonic imaging device according to an embodiment.

FIG. 2 is a diagram illustrating an example of the first ultrasonic image (structure enhanced image), the second ultrasonic image (speckle suppressed image), and an output image (filter processed image) according to the embodiment.

FIG. 3 (*a*) is a diagram showing an example of a window set in the first ultrasonic image and the second ultrasonic image, and FIG. 3 (*b*) is a diagram showing an example of a window set so as to partially overlap in the ultrasonic imaging device according to the embodiment.

FIG. 4 is an explanatory diagram illustrating a partial configuration of an ultrasonic CT device as an example of the ultrasonic imaging device according to the embodiment.

FIG. 5 (*a*) to FIG. 5 (*f*) are perspective views illustrating a shape of a transducer array of the ultrasonic CT device according to the embodiment.

FIG. 6 is a flowchart showing an operation of the ultrasonic imaging device according to the embodiment.

FIG. 7 is an explanatory diagram illustrating an example of an input screen displayed on an image display unit, which receives settings from a user, and a display screen of a filter processed image.

FIG. 8 is a diagram illustrating an incident wave, a reflected wave, and a transmitted wave transmitted from the ring-shaped transducer array according to the embodiment.

FIG. 9 is a block diagram illustrating a structure enhanced image generation processing according to the embodiment.

FIG. 10 is a block diagram illustrating the generation processing of the speckle suppressed image according to the embodiment.

FIG. 11 is a flowchart showing the operation of the ultrasonic imaging device according to the embodiment.

DESCRIPTION OF EMBODIMENTS

The ultrasonic imaging device according to an embodiment of the invention will be described using the drawings.

FIG. 1 is a block diagram showing a configuration of the ultrasonic imaging device 100 according to the present embodiment. FIG. 2 is a diagram illustrating an example of the first ultrasonic image, the second ultrasonic image, and an output image according to the embodiment.

As shown in FIG. 1, the ultrasonic imaging device 100 includes a transmission/reception unit 10, an image generation unit 20, and an image processing unit 30.

One or more transducer 1 is connected to the transmission/reception unit 10. The transmission/reception unit 10 outputs a transmission signal to one or more transducer 1. As a result, an ultrasonic wave is transmitted from the transducer 1 to the subject 2, and an ultrasonic echo is generated in the subject 2. The generated echo is received by the transducer 1, and the transducer 1 outputs a reception signal. The transmission/reception unit 10 receives a reception signal output from the transducer 1 and performs a predetermined processing such as an A/D conversion.

The image generation unit 20 generates the first ultrasonic image and the second ultrasonic image using the reception signal processed by the transmission/reception unit 10. The image generation unit 20 generates the image smoother than the first ultrasonic image as the second ultrasonic image. An example of the first ultrasonic image and the second ultrasonic image is illustrated in FIG. 2. The image generation unit 20 may include a first generation unit 21 that generates the first ultrasonic image and a second generation unit 22 that generates the smooth second ultrasonic image.

The image processing unit 30 calculates the filter coefficient using the pixel values of the corresponding pixels of the first ultrasonic image and the second ultrasonic image, and generates the output image by processing one of the first ultrasonic image and the second ultrasonic image according to the filter coefficient.

Since the second ultrasonic image is a smoother image than the first ultrasonic image, the speckle noise is reduced compared to the first ultrasonic image, but the contour of the tissue structure of the subject 2 tends to be more blurred than the first ultrasonic image. On the other hand, the speckle noise increases since the first ultrasonic image is not smoother than the second ultrasonic image, but the contour of the tissue structure of the subject 2 tends to appear clearly with high contrast. Thus, the image of the contour of the speckle noise and the tissue structure appropriately determine the filter coefficient using two types of the ultrasonic images that appear indifferent characteristics, and it is possible to generate an image in which the contour of the tissue structure is clear while reducing the speckle noise by processing either the first ultrasonic image or the second ultrasonic image using the filter coefficient.

Therefore, it is desirable that the first generation unit 21 of the image generation unit 20 generates the first ultrasonic image such that the boundary of the tissue structure of the subject 2 is enhanced, and the second generation unit 22 generates the second ultrasonic image such that speckle noise is reduced.

In order to obtain an output image by the image processing unit 30, it is desirable that the image processed according to the filter coefficient is a first ultrasonic image in which the contour of the tissue structure of the subject 2 appears clearly.

The image processing unit 30 uses coefficient a and constant b as filter coefficients, for example. A coefficient a and a constant b, with which the difference between a value ($aE_i+b$) and the pixel value $S_i$ of the corresponding i-th pixel of the second ultrasound image is as small as possible, are calculated by the image processing unit 30 using the pixel values $E_i$ and $S_i$ of the plurality of pixels in the window set for the first ultrasonic image and the second ultrasonic image, the value ($aE_i+b$) being obtained by multiplying the pixel value $E_i$ of the i-th pixel of the first ultrasonic image by the coefficient a and adding the constant b. The image processing unit 30 multiplies the pixel value $E_i$ of the pixel in the window of the first ultrasonic image by the calculated coefficient a and adds the constant b to obtain the pixel value of the output image $O_i$.

It is desirable that the image processing unit 30 sets a plurality of windows in the first ultrasonic image and the second ultrasonic image, and calculates a filter coefficient for each window. For example, as shown in FIG. 3(a), the window 23 is set in the first ultrasonic image and the second ultrasonic image without any gaps, and the filter coefficient is calculated and set for each window 23. It is necessary for the size of the window 23 to include a plurality of pixels since it is necessary to reflect the information of the structure included in the image in the filter coefficients a and b. Therefore, it is desirable to set a window so as to include two or more pixels.

For example, the image processing unit 30 can use an optimization method such as a least-square method to obtain a coefficient a and a constant b that give a minimum value of the difference between ($aE_i+b$) and $S_i$. When this optimization is executed, it is possible to stabilize the solution by adding a penalty term for stabilizing the solution, so it is possible to reduce the false image in the output image.

In addition, when performing the above-described optimization, the image processing unit 30 may calculate a solution that gives the minimum value using a sequential calculation method such as a steepest descent method, or may calculate a solution that gives the minimum value by analytical calculation if an analysis solution that gives the minimum value is obtained.

In addition, the degree of speckle reduction and the degree of clarification of the contour of the tissue boundary change according to the size of the window. When the window size is too small, the output image becomes equal to the speckle suppressed image, and if the window size is too large, the whole output image becomes a smoothed image. Therefore, for example, it is desirable to set various sizes of windows in advance using a plurality of ultrasonic images to calculate the filter coefficient to generate the output image, and it is desirable to determine an appropriate window size by using a method of selecting a window size having a large degree of reduction of the speckle and a large degree of clarification of the contour of the tissue boundary in advance, or a method of accepting a designation of the window size from a user, and the like.

In addition, as shown in FIG. 3 (b), the image processing unit 30 may set a plurality of windows 23 so as to partially overlap with each other. The pixel value of the output image is calculated using a value obtained by combining a plurality of coefficients a obtained respectively according to the overlapping windows 23 and a value obtained by combining a plurality of constants b in the pixels located in the overlapping region of the window 23. As the combination method, a desired method such as an average value, a maximum value, or a minimum value may be used.

The ultrasonic imaging device 100 of the embodiment may be configured as an ultrasonic CT device having a function of generating a transmitted wave image from the transmitted wave of the ultrasonic wave transmitted through the subject 2 as well as a function of generating the image by an echo of the ultrasonic wave. In this case, as shown in FIG. 1, one pair or more of the transducers 1 of the plurality of transducers 1 are disposed at positions facing each other across the subject 2. In this way, since the transducers 1 arranged facing each other can receive the transmitted wave of the ultrasonic wave transmitted to the subject 2, the image generation unit 20 can further generate the transmitted wave image of the subject 2 using the received signal of the transmitted wave.

Specific Embodiments

A specific configuration of the ultrasonic imaging device 100 of the embodiment will be described with reference to FIGS. 1 and 4. FIG. 4 illustrates a state in which the subject 2 is inspected by the ultrasonic imaging device 100. As illustrated in FIG. 4, an example in which the ultrasonic imaging device 100 is an ultrasonic CT device and particularly a device having a structure suitable for identifying a breast tissue will be described.

As shown in FIG. 1, the ultrasonic CT device (ultrasonic imaging device) 100 includes a control unit 50 in addition to the transmission/reception unit 10, the image generation unit 20, and the image processing unit 30. The transducer array 101 in which the transducer 1 is arranged in a ring shape is connected to the transmission/reception unit 10. An input unit 60 is connected to the control unit 50, and the image display unit 40 is connected to the image processing unit 30. Further, as illustrated in FIG. 4, the ultrasonic CT device 100 includes a bed 102 on which the subject 2 is placed and a cylindrical water tank 103 into which a chest can be inserted. The transmission/reception unit 10, the image generation unit 20, the image processing unit 30, and the control unit 50 are arranged in a space below the bed, although not illustrated in FIG. 4.

In the example in FIG. 4, the image display unit 40 has a touch panel structure and also serves as the input unit 60. In the bed 102, an opening is provided on a surface on which the subject 2 is mounted, and the water tank 103 is provided at a lower part of the opening. As illustrated in FIG. 5(a), a ring-shaped transducer array 101 and a driving unit 202 that moves the transducer array 101 in the axial direction (vertical direction) of the water tank 103 are arranged inside the water tank 103. The water tank 103 is filled with deaerated and purified hot water. A thermometer (not shown) is provided in a lower part of the water tank 103. Further, a heating device and a deaerator (not shown) that heat and deaerate water are connected to the water tank 103. The thermometer, the heating device, and the deaerator are connected to the control unit 50.

An imaging condition of the ultrasonic CT device are set by a user through the touch panel of the input unit 60 or the like.

The transmission/reception unit 10, the image generation unit 20, the image processing unit 30, and the control unit 50 may be configured to realize each of the functions by a software, or realize a part or all of the functions by hardware. In the case of realizing by software, each unit is configured to include a processor (for example, a Central Processing Unit (CPU) or Graphics Processing Unit (GPU)), and a memory in which a program is stored in advance, and the processor realizes the functions by reading and executing the program. In the case of realizing by hardware, for example, a part or whole of each unit is constituted using a custom. IC such as Application Specific Integrated Circuit (ASIC) or a programmable IC such as Field-Programmable Gate Array (FPGA), and a circuit design may be performed so as to realize the operation.

The operation of the ultrasonic CT device 100 will be described below using the flowchart of FIG. 6.

For the ultrasonic CT device in the embodiment, when the power is turned on, the control unit 50 takes in the temperature of the water in the water tank 103 from the thermometer, heats the water by the heating device until the temperature of the water reaches a predetermined temperature (about body temperature), and deaerates the water by the deaerator. Thus, the water tank 103 is filled with deaerated water adjusted to a predetermined temperature. In a state in which the subject 2 is not inserted into the water tank 103, the control unit 50 transmits and receives the ultrasonic wave under predetermined conditions, and acquires in advance the reception data before the subject 2 is inserted.

As illustrated in FIG. 7, the control unit 50 causes the image display unit 40 to display a screen that receives a type of an image to be captured from a user (subject 2 or operator), and receives a type of the image to be captured via the input unit 9. In the example in FIG. 7, as the image types, a button 61 for selecting a filter processed image, a button 62 for selecting a speckle suppressed image, and a button 63 for selecting a structure enhanced image are displayed on the image display unit 40, and the user can select the image type by the input unit 9 that is the touch panel.

Here, the speckle suppressed image is the second ultrasonic image described above, and is an image generated by an image generation method such as a spatial compound for reducing speckle, an image subjected to image processing such as smoothing processing for reducing speckle with respect to an image once generated by beam forming by an image generation method such as the delay addition method. The structure enhanced image is the above-described first ultrasonic image, and is an image obtained by beam forming by the delay addition method, or a once generated image subjected to the process of further enhancing the boundary or the like by the delay addition method or the like. The structure enhanced image may be an image in which the contour of the tissue structure of the subject 2 clearly appears with high contrast, and is not limited to an image subjected to image processing such as boundary enhancement processing. The filter processed image is an image generated by the image processing unit 30 calculating a filter coefficient using pixel values of corresponding pixels of the first ultrasonic image and the second ultrasonic image, and processing one of the first ultrasonic image and the second ultrasonic image using a filter coefficient. Thus, the filter processed image is an image with a clear tissue structure while reducing speckle.

When the user selects an image of the type generated by the image display unit 40 by pressing any one of the buttons 61, 62, and 63, the control unit 50 displays a display prompting the subject 2 to lie on the bed 102 and to insert one breast into the water tank 103 on the image display unit 40. If the control unit 50 confirms that the breast of the subject 2 is inserted into the water tank 103 by operating the input unit 60 by the subject 2, the control unit 50 transmits and receives the ultrasonic waves from the transducer array 101 to the subject 2 (step 501). Specifically, under the control of the control unit 50, the transmission/reception unit 10 generates the transmission signal based on a condition input from the input unit 60 or a predetermined imaging condition, and outputs the transmission signal to one or a plurality of transducers 1 constituting the transducer array 101. As a result, as illustrated in FIG. 8, an ultrasonic wave (incident wave) is transmitted from the one or a plurality of transducers 1 a having received the transmission signal toward the subject 2.

As illustrated in FIG. 8, the reflected wave reflected by the subject 2 is received by the plurality of transducers 1 in a predetermined angular range (reception aperture) around the transducer 1 as a center that transmitted the ultrasonic wave. The transducer 1 that received the reflected wave outputs each received signal of the reflected wave, and the received signal of the reflected wave is input to the transmission/reception unit (step 502). On the other hand, the transmitted wave that transmitted through the subject 2 is received by the plurality of transducers 1 in a predetermined angular range facing the one or a plurality of transducers 1 that transmitted the ultrasonic waves. The transducer 1 that received the transmitted wave outputs each received signal of the transmitted wave, and the received signal of the transmitted wave is input to the transmission/reception unit 10. The transmission/reception unit 10 repeatedly transmits and receives the ultrasonic waves for each predetermined transmission angle (view) by shifting the position of the transducer 1 that outputs the transmission signal. In addition, the driving unit 202 shifts the transducer 101 to the predetermined position and repeats the transmission and reception of the ultrasonic waves for each similarly predetermined view.

The transmission/reception unit 10 converts the received signal (RF signal) into a digital signal by sampling.

When the selection button of the image type accepted by the input unit 60 is the button 61 that selects the filter processed image (step 503), the control unit 50 causes image generation unit 20 to generate the structure enhanced image E and the speckle suppressed image S (step 504), and generates a filter processed image using the structure enhanced image E and the speckle suppressed image S (step 505).

First, as illustrated in FIG. 9, the first generation unit 21 of the image generation unit 20 obtains the signal intensity of each pixel by performing phase addition of the received signals of all the transducers 1 in the reception aperture 80 of the reflected wave according to the delay addition method (Delay and Sum, DAS), and generates the structure enhanced image E (first ultrasonic image) in which the contour of the tissue structure clearly appears with high contrast. As illustrated in FIG. 10, the second generation unit 22 generates the plurality of ultrasonic images by performing phase addition by the sub-aperture delay addition method, and by combining the plurality of ultrasonic images, generates an image S (second ultrasonic image) in which the speckle noise is reduced by the spatial compounding effect (step 504).

The first generation unit 21 will be further described in more details. As illustrated in FIG. 9, the first generation unit 21 includes a delay addition unit 121. The first generation unit receives the reception signals (RF signals) of all the transducers 1 in the reception aperture 80 of the reflected wave from the transmission/reception unit 10. The first generation unit 21 divides the sum of the distance from the transmitted transducer 1$a$ to the point (reception focus in the subject 2) corresponding to the pixel of interest in the subject 2 and the distance from the point of the pixel of interest to the received transducer 1 by the sound velocity of the ultrasonic wave (for example, the sound velocity of water), thereby obtaining the time (timing) until the reflected wave (echo) from the point of the pixel of interest returns to the transducer 1 after the transducer 1$a$ transmits the ultrasonic wave (incident wave). Since the distance between the point of the pixel of interest and the transducer 1 is different for each position of the transducer 1 that receives the echo, the above-described time (timing) is also different for each transducer 1. The first generation unit 21 obtains a delay amount of delaying the reception signal of each transducer for each pixel of interest such that the reflected wave reflected by the pixel of interest in the subject 2 can be added using all the timing of the received signal received by each transducer 1. Alternatively, the first generation unit 21 reads the delay amount obtained in advance. The delay addition unit 121 of the first generation unit 21 delays the reception signal output from the transducer 1 by the above-described delay amount for each pixel of interest in the subject 2, thereafter adds the reception signal (phasing addition), and sets the signal intensity after addition to the value of the pixel (delay addition method). By performing this on all the pixels in the field of view, an ultrasonic image (B mode image) can be generated. The generated B-mode image is output as the structure enhanced image E (first ultrasonic image) in which the contour of the tissue structure appears clearly with high contrast. The reflected image generation unit 25 may generate a B-mode image for each view, and may use the image obtained by adding these images as the structure enhanced image E.

On the other hand, as illustrated in FIG. 10, the second generation unit 22 includes a plurality of delay addition units 121, 122, and 123, and one addition unit 124. The processing of the second generation unit 22 divides the reception aperture 80 (multi-look), and receives, for each reception aperture 81, 82, and 83 after division, the reception signal of the transducer 1 in the reception aperture 81, 82, and 83 from the transmission/reception unit 10. Each of the delay addition units 121, 122 and 123 performs phase addition of the reception signal of the transducer 1 of the reception aperture 81, 82 and 83 by the delay addition method for each point (reception focal point) corresponding to the pixel of interest in the field of view. As a result, the ultrasonic image (B mode image) with the signal intensity after the phase addition as the pixel value can be generated for each of the reception apertures 81, 82, and 83. Since the positions of the reception apertures 81, 82 and 83 are different in these B-mode images, the pattern of speckle noise is different. The addition unit 124 of the second generation unit 22 can generate an image S (second ultrasonic image) in which speckle noise is reduced by the spatial compounding effect by adding these B-mode images incoherently, that is, by adding the B-mode images without maintaining the phase information (step 504).

Next, the image processing unit 30 calculates the filter coefficient using the structure enhanced image E and the speckle suppressed image S generated in step 504, and filter processes the structure enhanced image E using the calculated filter coefficient to generate a filter processed image. As a result, it is possible to generate the filter processed image in which the speckle is reduced and the contour of the tissue structure is clear. This process will be described in detail with reference to the flow of FIG. 11.

The image processing unit 30 sets a plurality of windows 23 at positions corresponding to the structure enhanced image E and the speckle suppressed image S as shown in FIG. 3 (a), for example (step 1001). The windows may be set so as to partially overlap with each other as shown in FIG. 3 (b). The size (number of pixels m) and the shape of the window 23 may be a predetermined size (number of pixels) and shape, or a size (number of pixels) and a shape received from the user via the input unit 60 if the size includes two or more pixels as described above.

Equation (1) representing the i-th pixel value $O_i$ of the output image is obtained for all the pixels in the kth window 23 using the pixel value $E_i$ of the i-th pixel in one kth window 23 of the structure enhanced image E, and the coefficient $a_k$ and the constant $b_k$ of the filter coefficient. In addition, expression (2) representing the i-th pixel value $O_i$ of the output image is obtained for all the pixels in the kth window 23 using the pixel value $S_i$ of the i-th pixel in the kth window 23 of the speckle reduced image S and unnecessary value $n_i$ such as noise for each pixel. As a result, equation (1) and equation (2) equal in number to the number of pixel m in the kth window are obtained.

$$O_i = a_k E_i + b_k \tag{1}$$

$$O_i = S_i - n_i \tag{2}$$

The image processing unit 30 calculates, by obtaining the solution in which $n_i$ is minimized, the coefficient $a_k$ and the constant $b_k$ determined for the kth window and $n_i$ determined for each pixel using m equation (1) and equation (2), respectively. As a result, the filter coefficients (coefficient $a_k$, constant $b_k$, and $n_i$) for the window are calculated (step 1002). For example, the image processing unit 30 calculates the filter coefficients using the optimization method such as the least-square method.

This is repeated until the filter coefficients are obtained for all the windows 23 (step 1003). Further, as shown in FIG. 3 (b), when the windows 23 are set partially overlapped, the average value of each of the coefficient $a_k$ and the constant $b_k$ of the overlapping window is obtained and set as the coefficient $a_k$ and the constant $b_k$ of the pixel of the overlapping region.

The structure enhanced image E is processed with the filter coefficient for each window to generate a filter processed image (output image) O (step 1004). Specifically, the pixel value $O_i$ of the filter processed image (output image) O is calculated by calculating the equation (1), using the pixel value $E_i$ of the structure enhanced image E and the filter coefficients (coefficient $a_k$ and constant $b_k$) of the window 23 to which the pixel belongs.

This filter process transfers a remarkable structure of the structure enhanced image E to the speckle suppressed image S, and has an effect of smoothing the speckle suppressed image with respect to a part having no significant structure in the structure enhanced image. As a result, it is possible to generate a filter processed image (output image) that achieves both the reduction of the speckle and the clarification of the contour image of the tissue structure.

The image generation unit 30 proceeds to step 506 in FIG. 6, and outputs and displays the filter processed image generated in step 505 on the image display unit 40.

On the other hand, if the selection button of the image type accepted from the user by the input unit 60 is not the button 61 for selecting the filter processed image in step 503, the process proceeds to step 507. If the user presses the button 63 for selecting the structure enhanced image E in step 507, the image generation unit 20 generates the structure enhanced image E in step 508. The generate processing of the structure enhanced image E is as described in step 504. Then, the process proceeds to step 509, in which the image processing unit 20 displays the structure enhanced image E on the image display unit 40.

If the user presses the button 63 for selecting the speckle suppressed image S in step 507, the process proceeds to step 510, and the image generation unit 20 generates the speckle suppressed image by the processing method described in step 504. Then, in step 511, the image processing unit 20 displays the speckle suppressed image S on the image display unit 40.

As described above, the ultrasonic CT device 100 according to the embodiment can display any one of the filter processed image, the structure enhanced image E, and the speckle suppressed image S that achieves both speckle reduction and clarification of contour image of tissue structure at the same time by the selection of the user.

When the transducer array 101 is moved to a predetermined position (slice) by the driving unit 202 and the reflected wave signal is received, the processing in FIG. 6 described above can be performed for each slice to generate a three-dimensional ultrasonic image (volume data).

The ultrasonic CT device 100 can also generate a transmitted wave image (attenuation rate image, sound velocity image) of the subject 2 using the received signal of the transmitted wave. This will be briefly described below.

The image generation unit 20 obtains an amplitude of each transducer 1 for the transmission signal received in a state in which the subject 2 is inserted in each view. On the other hand, the image generation unit 20 obtains the amplitude of the received signal of each transducer 1 received without inserting the subject 2. The image generation unit 20 calculates a difference in logarithm of the amplitude before and after the insertion of the subject 2 for each view and each reception channel. This collection of data is referred to as a sinogram. The image generation unit 20 reconstructs a tomographic image of the subject 2 by processing the sinogram of the difference in the logarithm of the amplitude with Filtered Back Projection (FBP) or the like widely used in the field of X-ray CT. Thus, a distribution image of the difference in the attenuation rate before and after insertion of the subject 2 is obtained. The image generation unit uses a predetermined value (estimated value) as the attenuation rate of water, thereby generates an image (attenuation image) that shows the attenuation rate (unit: dB/MHz/cm) distribution of the subject 2 from the distribution image of the difference in the attenuation rate.

The image generation unit 20 performs Hilbert transformation in the time direction with respect to the transmission signal output from each transducer 1 in each view, and obtains the reception timing of the maximum amplitude of the received wave. The image generation unit 20 similarly obtains the reception timing of the maximum amplitude for the reception signals of each transducer 1 received before the insertion of the subject 2. The image generation unit 20 calculates the difference in reception timing before and after the insertion of the subject 2 for each view and each reception channel respectively to obtain the sinogram. The image generation unit 20 reconstructs the tomographic image by processing the sinogram of a difference in reception timing by a filter correction inverse projection method or the like. This tomographic image is the distribution image of the difference in "Slowness" of the ultrasonic wave before and after insertion of the subject 2. The "Slowness" is the reciprocal number of the sound velocity. The image generation unit 20 generates a distribution image (sound velocity image) of the sound velocity of the subject 2 from the distribution image of the difference of "Slowness" using the sound velocity value (estimated value) of water.

A three-dimensional attenuation image and/or a sound velocity image can be generated by repeating the generation of the attenuation image and/or the generation of the sound velocity image for each slice in which the transducer array 101 is moved by the driving unit 202.

According to the selection by the user, the ultrasonic imaging device (ultrasonic CT device) of the embodiment can generate one or more image of the filter processed image, the structure enhanced image E, and the speckle suppressed image S that achieves both speckle reduction and clarification of contour image of tissue structure, and the attenuation image and the sound velocity image, and display the images on the image display unit. Therefore, the ultrasound imaging device can assist the doctor in diagnosing the presence or absence of a tumor included in the tissue structure of the subject 2 by these images.

In the above-described embodiment, an example in which the ring-shaped transducer array 101 as illustrated in FIG. 5 (a) is used is described as the transducer array 101 of the ultrasonic CT device capable of generating a transmitted wave image, but it is not limited to the ring shape, and it suffices that at least some of the transducers 1 are opposed to each other across the subject 101. For example, as illustrated in FIGS. 5(d) to 5(f), it is possible to use the transducer array 204 in which the transducers 1 are arranged in a basket shape, a semicircular transducer array 205, and two transducer arrays 206 arranged to face each other. As illustrated in FIG. 5 (c), it is also possible to use a two-dimensional ring-shaped transducer array 203 in which the transducer array is arranged in the axial direction (depth direction) of the water tank 103. Further, as illustrated in FIG. 5 (b), the driving unit 202 may not only move the ring-shaped transducer array 101 in the axial direction of the water tank 103 but also move the transducer array 101 in a tilting direction. Further, in the case of using the semicircular transducer array 205, it is also possible to widen the angular range in which the transmitted wave signal can be received by moving the transducer array 205 in the circumferential direction by the driving unit 202.

REFERENCE SIGN LIST

1: transducer
2: subject
9: input unit
10: transmission/reception unit
20: image generation unit
21: first generation unit
22: second generation unit
30: image processing unit
40: image display unit
50: control unit
60: input unit
100: ultrasonic imaging device (ultrasonic CT device)
101: transducer array
102: bed
103: water tank

The invention claimed is:

1. An ultrasonic imaging device, comprising:
a processor coupled to a memory storing instructions that when executed configure the processor to:
transmit an ultrasonic wave from one or more transducers to a subject by outputting a transmission signal to the one or more transducers, at the same time receive a reception signal output by the plurality of transducers that received an echo generated in the subject and perform a predetermined processing;
generate a first ultrasonic image and a second ultrasonic image using the processed reception signal;
generate and output an output image using the first ultrasonic image and the second ultrasonic image,
generate the second ultrasonic image which is smoother than the first ultrasonic image,
generate the output image by calculating filter coefficients using pixel values of corresponding pixels of the first ultrasonic image and the second ultrasonic image, and process one of the first ultrasonic image and the second ultrasonic image by the filter coefficients, wherein the processor is further configured to:
use a coefficient a and a constant b as the filter coefficients,
calculate the coefficient a and the constant b, with which a difference between a value obtained by multiplying a pixel value of a pixel of the first ultrasonic image by the coefficient a and adding the constant b and the pixel value of the corresponding pixel of the second ultrasound image is minimum, using the pixel values of a plurality of pixels in a window set for the first ultrasonic image and the second ultrasonic image, and
calculate a pixel value of the output image by multiplying the pixel value of the pixel in the window of the first ultrasonic image by the calculated coefficient a and the constant b.

2. The ultrasonic imaging device according to claim 1, wherein the processor is further configured to:
generate the first ultrasonic image such that a boundary of a tissue structure of the subject is enhanced, and
generate the second ultrasonic image such that a speckle noise is reduced.

3. The ultrasonic imaging device according to claim 1, wherein the processor is further configured to process the first ultrasonic image by the filter coefficients.

4. The ultrasonic imaging device according to claim 1, wherein the processor is further configured to set a plurality of windows in the first ultrasonic image and the second ultrasonic image, and calculate the filter coefficients for each window.

5. The ultrasonic imaging device according to claim 4, wherein the processor is further configured to set the plurality of windows so as to partially overlap with each other, and calculate a pixel value of the output image using a value obtained by combining the coefficient a and the constant b obtained for the overlapping windows for the pixels located in the region where the windows overlap.

6. The ultrasonic imaging device according to claim 1, wherein at least one pair of the plurality of transducers are disposed at positions facing each other across the subject, and may receive a transmitted wave of the ultrasonic wave transmitted to the subject, and
wherein the processor is further configured to generate a transmitted wave image of the subject using the reception signal of the transmitted wave.

7. The ultrasonic imaging device according to claim 1,
wherein the plurality of transducers are arranged in an array,
wherein the processor is further configured to generate the first ultrasonic image by delaying and adding the reception signals output from the plurality of transducers in the reception aperture set in advance, and
wherein the processor is further configured to divide the reception aperture into a plurality of sub reception apertures, and delay and add the reception signals output from the plurality of transducers in the sub reception aperture, for each sub reception aperture, thereby generating the second ultrasonic image by obtaining ultrasonic images for each sub reception aperture and combining the obtained ultrasonic images for each sub reception aperture.

8. An image processing device, comprising:
a processor coupled to a memory storing instructions that when executed configure the processor to:
generate a first ultrasonic image and a second ultrasonic image by receiving a reception signal output by a plurality of transducers that received an echo generated in a subject transmitted with an ultrasonic wave, or an ultrasonic image generated from the reception signal;
generate and output an output image using the first ultrasonic image and the second ultrasonic image,
generate the second ultrasonic image which is smoother than the first ultrasonic image, and
generate the output image by calculating filter coefficients using pixel values of corresponding pixels of the first ultrasonic image and the second ultrasonic image, and
process one of the first ultrasonic image and the second ultrasonic image by the filter coefficients,
wherein the processor is further configured to:
use a coefficient a and a constant b as the filter coefficients,
calculate the coefficient a and the constant b, with which a difference between a value obtained by multiplying a pixel value of a pixel of the first ultrasonic image by the coefficient a and adding the constant b and the pixel value of the corresponding pixel of the second ultrasound image is minimum, using the pixel values of a plurality of pixels in a window set for the first ultrasonic image and the second ultrasonic image, and
calculate a pixel value of the output image by multiplying the pixel value of the pixel in the window of the first ultrasonic image by the calculated coefficient a and the constant b.

* * * * *